United States Patent
Velez Wiesner

(10) Patent No.: US 11,931,235 B1
(45) Date of Patent: *Mar. 19, 2024

(54) EXTERNAL MALE INCONTINENCE CLAMP

(71) Applicant: Wiesner Healthcare Innovations LLC, Miami, FL (US)

(72) Inventor: Juan Felipe Velez Wiesner, Medellin (CO)

(73) Assignee: Wiesner Helathcare Innovation, LLC, Hialeah, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/191,436

(22) Filed: Mar. 28, 2023

Related U.S. Application Data

(63) Continuation of application No. 16/810,148, filed on Mar. 5, 2020, now Pat. No. 11,642,205, which is a continuation of application No. 15/253,051, filed on Aug. 31, 2016, now Pat. No. 10,624,728.

(51) Int. Cl.
*A61F 2/00* (2006.01)

(52) U.S. Cl.
CPC .... *A61F 2/0054* (2013.01); *A61F 2220/0091* (2013.01)

(58) Field of Classification Search
CPC .. A61F 2220/0091; A61F 2/0054; A61F 2/00; A61F 2/0004; A61F 2/0009; A61F 2/0013; A61F 2/0018; A61F 2/0031; Y10S 128/25; A61B 17/122; A61B 17/1322
USPC ............ 128/885, DIG. 25, 842; 600/29; 606/151, 157, 201; D24/143
See application file for complete search history.

(56) References Cited

U.S. PATENT DOCUMENTS

| | | | |
|---|---|---|---|
| 2,756,753 A | 7/1956 | Means | |
| 3,203,421 A * | 8/1965 | Bialick | A61F 2/0054 24/514 |
| 7,658,195 B2 | 2/2010 | Dennis | |
| 11,642,205 B2 * | 5/2023 | Velez Wiesner | A61F 2/0054 128/885 |
| 2002/0111640 A1 | 8/2002 | Krause | |
| 2004/0129277 A1 * | 7/2004 | Parkes | A61F 2/0054 128/885 |

OTHER PUBLICATIONS

KindKlamp™ _ Bioderm Inc.; https://bioderminc.com/product/kind-klamp/, accessed Jul. 20, 2023.
UriLok™ Male Urinary Incontinence Clamp—iMEDiHelp; https://www.imedihelp.com/product/urilok-male-urinary-incontinence-clamp/, accessed Jul. 20, 2023.
JeatoMed I Incontinence Care for Men—JEATOMED; https://jeatomed.com/, accessed Jul. 20, 2023.

* cited by examiner

*Primary Examiner* — Caitlin A Carreiro
(74) *Attorney, Agent, or Firm* — Squire Patent Consulting & IP Law LLC; Brendan E. Squire

(57) ABSTRACT

An incontinence clamp is provided. The incontinence clamp includes an upper clamp arm and a lower clamp arm. Each of the upper and lower clamp arms include a first end, a second end, an inner surface and an outer surface. The inner surfaces face each other. A hinge pivotally connects the first ends of the upper and lower clamp arms together. An upper guide is coupled to the inner surface of the upper clamp arm and a lower guide is coupled to the inner surface of the lower clamp arm. A connector releasably connects the second ends of the upper clamp arm and the lower clamp arm together.

20 Claims, 4 Drawing Sheets

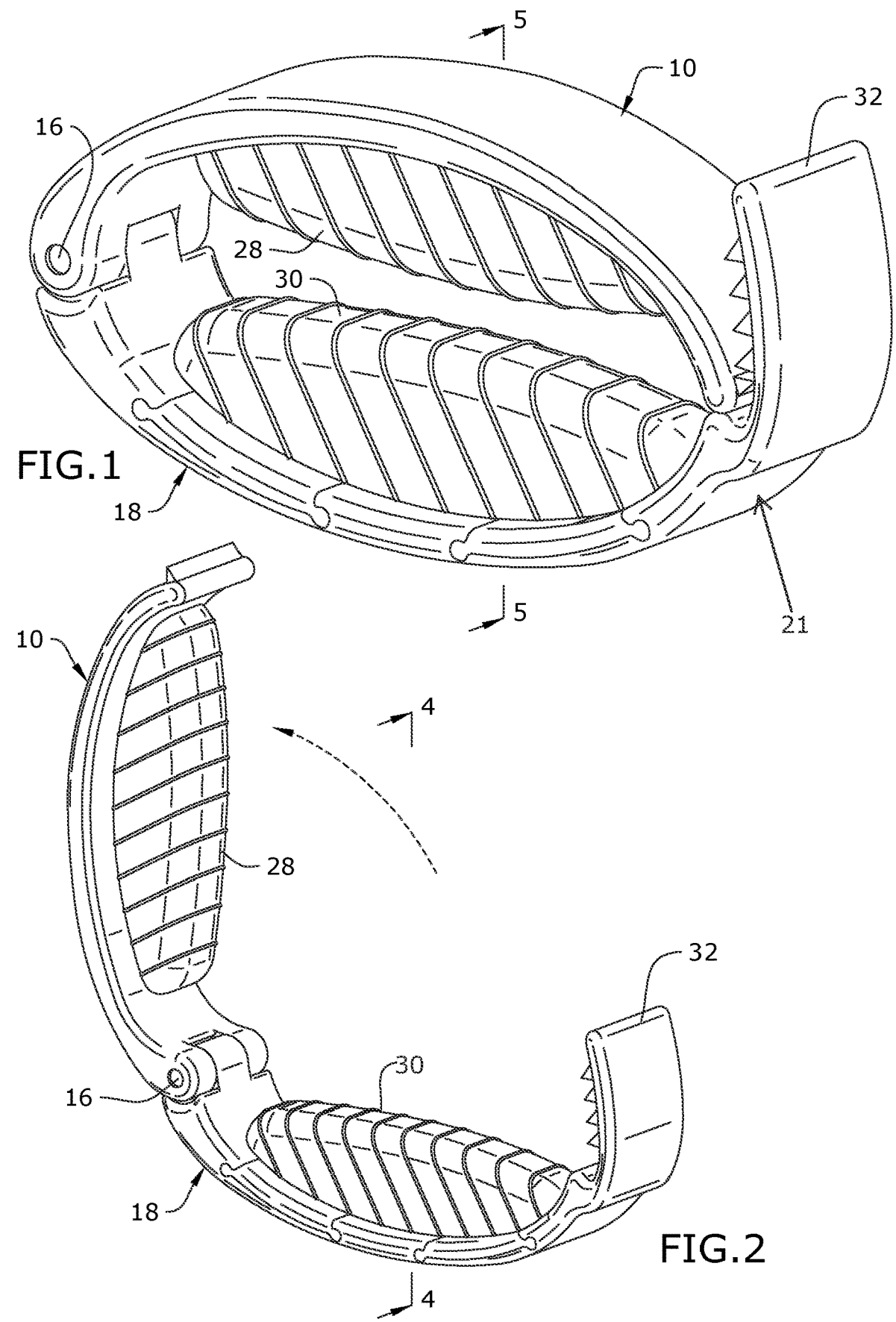

EXTERNAL MALE INCONTINENCE CLAMP

CROSS-REFERENCE TO RELATED APPLICATIONS

This application is a continuation of U.S. non-provisional application Ser. No. 16/810,148, filed Mar. 5, 2020, which is a continuation of Ser. No. 15/253,051, filed Aug. 31, 2016, issued as U.S. Pat. No. 10,247,728 on Apr. 21, 2020, the contents of which are herein incorporated by reference.

BACKGROUND OF THE INVENTION

The present invention relates to incontinence prevention and, more particularly, to an external male incontinence clamp.

Incontinence is a problem encountered by many men and is more common among geriatrics. While the cause of male incontinence may have a variety of different reasons, the uncontrolled and undesired passage of urine is a significant problem resulting in embarrassment, restriction of activities and depression.

While adult diapers are one solution to the problem, they are bulky, retain the moisture, and are embarrassing and difficult for some aging men to handle. Other incontinence clamps have been developed over the years, but since anatomies is different between individuals, it is difficult to create a good fit between the device and the penis. This causes the devices to be extremely uncomfortable and ineffective.

Most of the incontinence clamps developed use foam pads as the interface material between the device and the skin. This creates irritation and swelling of the skin. When the foam collects urine, it is very difficult to clean and makes the device smell bad. Some other clamps include Polivynilsiloxane pads. This material is much better than foam but given the properties of the material, it will release natural oil which acts as lubricant and causes the clamp to slip out of position.

As can be seen, there is a need for an improved male incontinence clamp which retains on the penis during everyday activities, that adapts to the anatomy of the patient, that is easy for older men to use and provides control of incontinence without causing irritation or swelling of the tissue.

SUMMARY OF THE INVENTION

In one aspect of the present invention, an incontinence clamp comprises an upper clamp arm comprising a first end, a second end, and a first arcuate inner surface dimensioned to partially encircle a penis of a user. A lower clamp arm comprises a first end, a second end, and a second arcuate inner surface dimensioned to partially encircle the penis of the user. A hinge pivotably connects the first end of the upper clamp arm with the first end of the lower clamp arm. A removable upper guide is dimensioned to span the first arcuate inner surface. The removable upper guide comprises a curved concave inner surface, a convex outer surface, and an upper attachment removably coupling the removable upper guide with the upper clamp arm. An upper padding is shaped as a cover that is sized to be secured over the removable upper guide, exclusive of the upper attachment. A lower guide is dimensioned to span the second arcuate inner surface of the lower clamp arm. The lower guide comprises a first side portion, a second side portion and a middle portion disposed in between the first side portion and the second side portion. The middle portion comprises a protrusion oriented towards the upper clamp arm. A lower attachment couples the lower guide with the lower clamp arm. A lower padding is shaped as a cover that is sized to be secured over the lower guide, exclusive of the lower attachment.

These and other features, aspects and advantages of the present invention will become better understood with reference to the following drawings, description, and claims.

BRIEF DESCRIPTION OF DRAWINGS

FIG. 1 is a perspective view of an embodiment of the present invention shown in a closed configuration;

FIG. 2 is a perspective view of an embodiment of the present invention shown in an open configuration;

DETAILED DESCRIPTION OF THE INVENTION

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

The present invention includes an external male incontinence clamp. When the clamp is placed on the penis, the device occludes the urethra while promoting blood circulation. The clamp of the present invention includes guides that adapt the user anatomy in shape and size. The material used is biocompatible, does not cause irritation or swelling, promotes a good perspiration of the skin and does not slip off of the penis.

Figure 3:
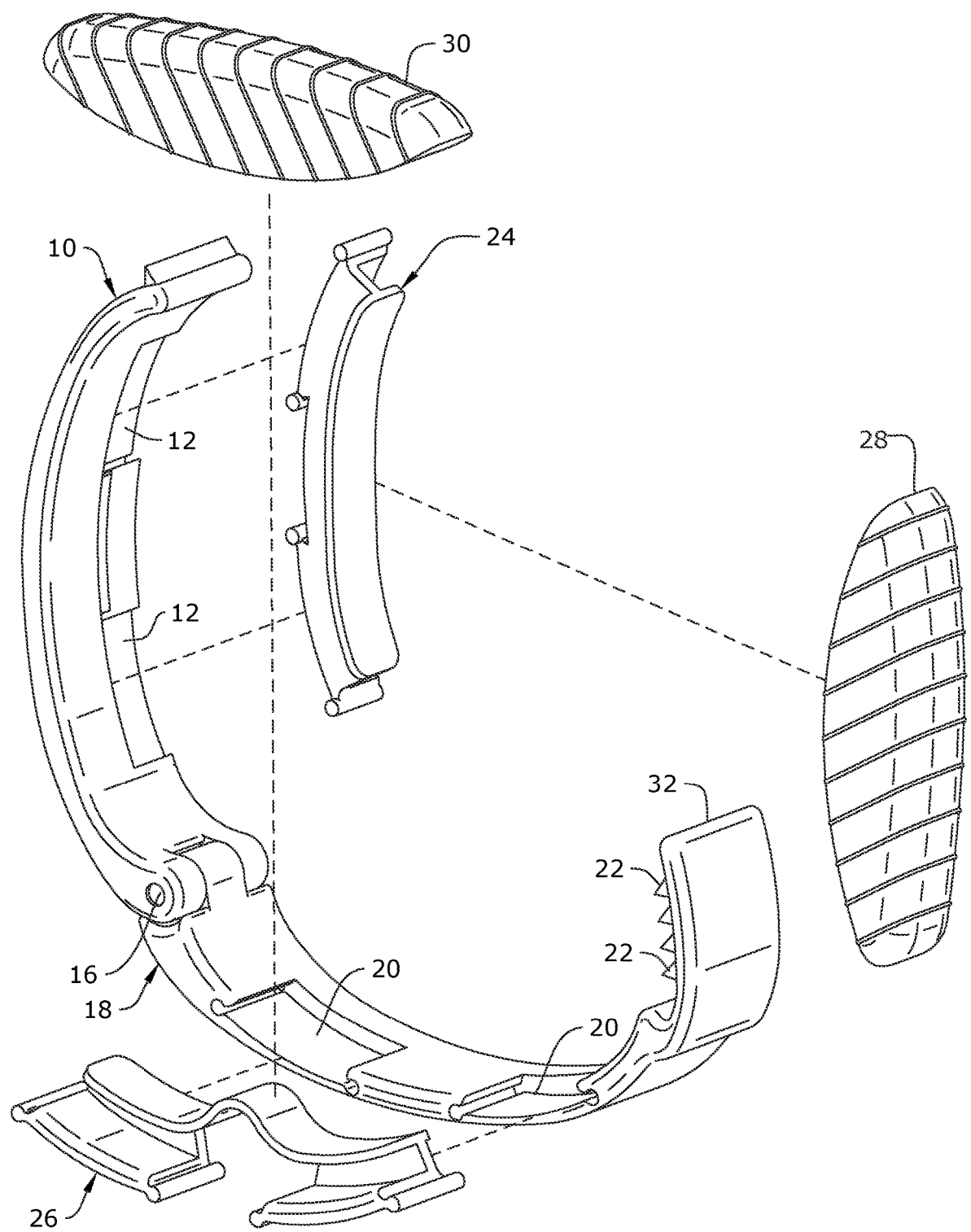
FIG. 3 is an exploded view of an embodiment of the present invention.
Figure 4:
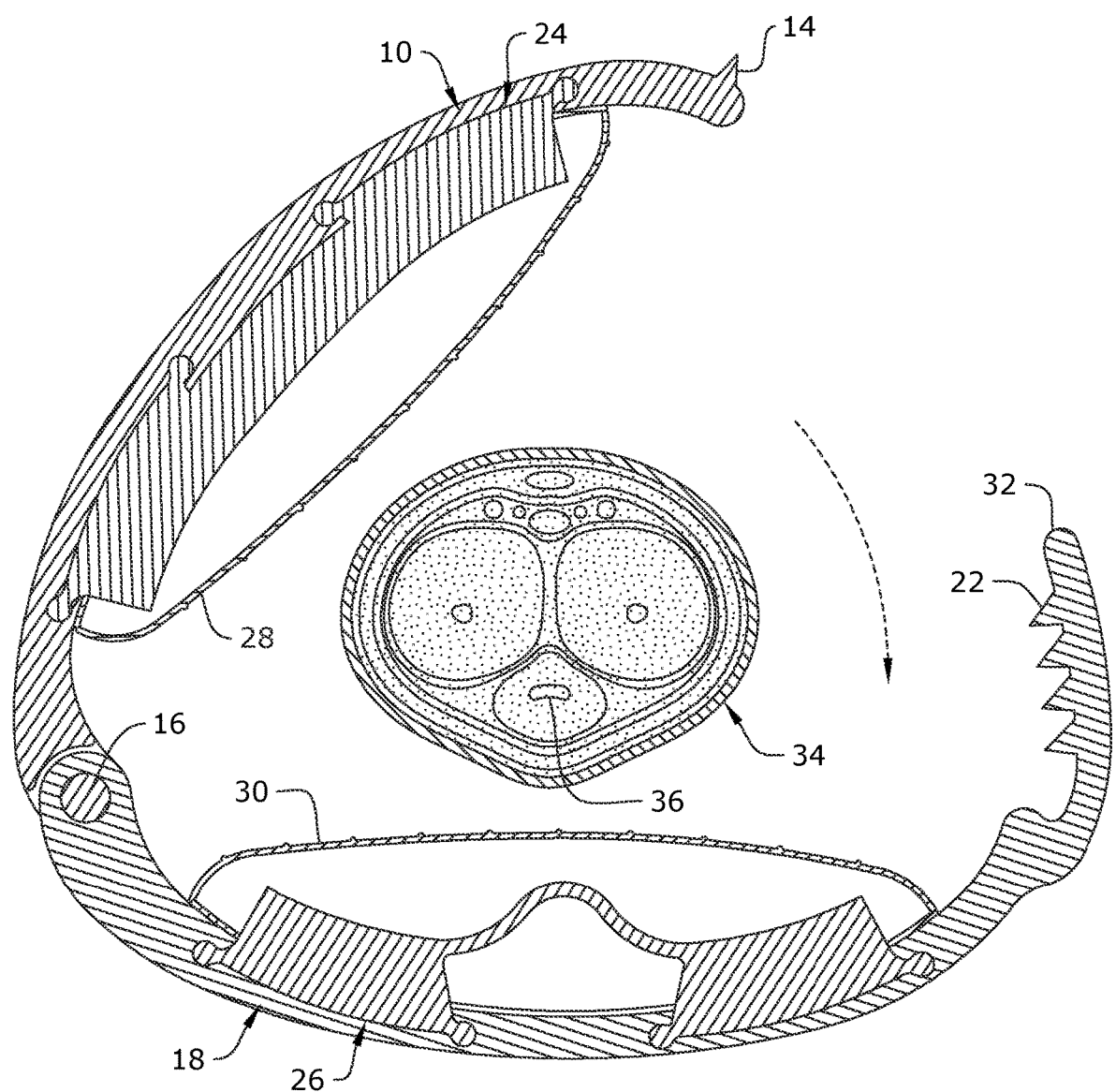
FIG. 4 is a section view of the present invention taken along line 4-4 in FIG. 2.
Figure 5:
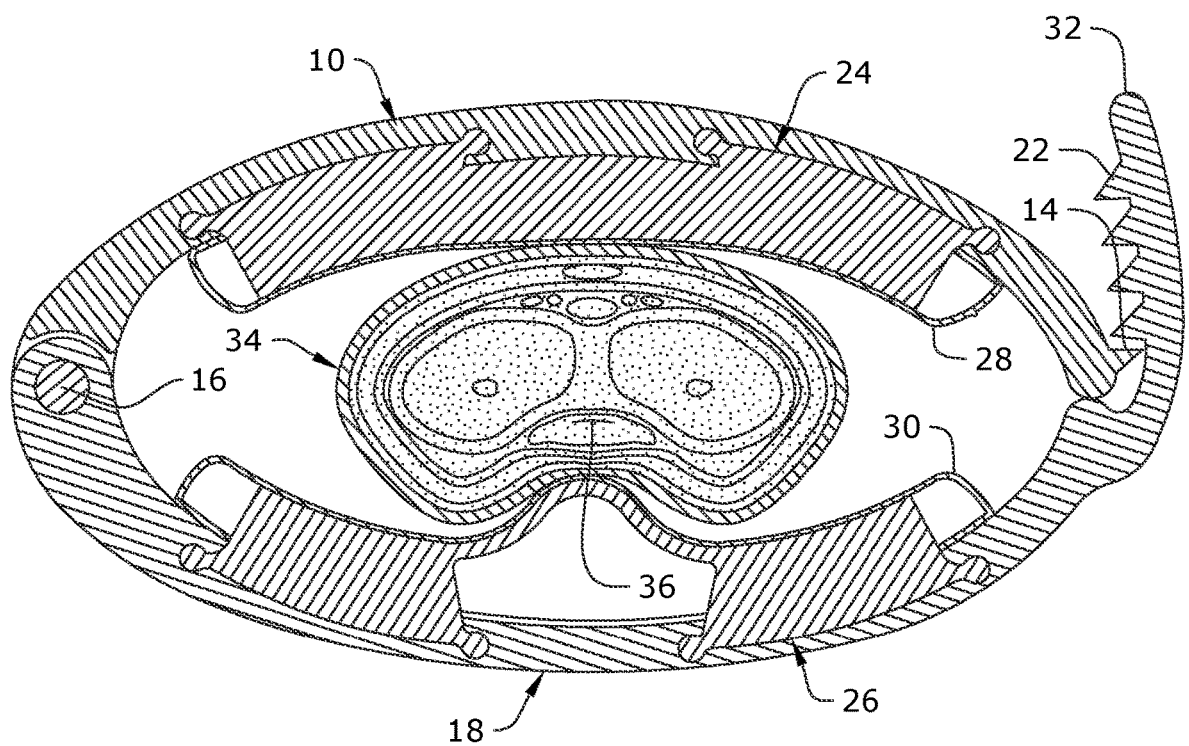
FIG. 5 is a section detail view of the present invention taken along line 5-5 in FIG. 1.

Referring to FIGS. 1 through 5, the present invention includes an incontinence clamp. The incontinence clamp includes an upper clamp arm 10 and a lower clamp arm 18. Each of the upper and lower clamp arms 10, 18 include a first end, a second end, an inner surface and an outer surface. The inner surfaces face each other. A hinge 16 pivotally connects the first ends of the upper and lower clamp arms 10, 18 together. An upper guide 24 is coupled to the inner surface of the upper clamp arm 10 and a lower guide 26 is coupled to the inner surface of the lower clamp arm 18. A connector 21 releasably connects the second ends of the upper clamp arm 10 and the lower clamp arm 18 together.

The upper guide 24 and lower guide 26 contours to the penis 34 and applies pressure to the urethra 36, preventing incontinence. The upper guide 24 includes a curved concave inner surface. The lower guide 26 includes a first side portion, a second side portion and a middle portion disposed in between the first side portion and the second side portion. The middle portion includes a curved convex portion protruding towards the upper clamp arm 10. The first side portion and the second side portion may each include a curved concave inner surface curving in the opposite direction of the middle portion. The upper guide 24 and the lower guide 26 may be formed of a rigid polymer to provide appropriate pressure to the penis 34. For example, the rigid polymer is acrylonitrile butadiene styrene.

In certain embodiments, the upper guide 24 and the lower guide 26 are releasably attached to the inner surface of the upper clamp arm 10 and lower clamp arm 18 respectively. Since the upper and lower guides 24, 26 may be removable, a user may replace the guides 24, 26 depending on the size of the penis 34. In such embodiments, a slot 12 may be formed on the inner surface of the upper clamp arm 10. The upper clamp guide 24 includes a ridge releasably retained within the slot 12. A slot 20 may be formed on the inner surface of the lower clamp arm 18. The lower clamp guide 26 includes a ridge releasably retained within the slot 20.

The present invention may further include a padding 28, 30. An upper padding 28 may be secured to the upper clamp arm 10 and a lower padding 30 may be secured to the lower clamp arm 18. The padding 28, 30 may be in the shape of a cover and is sized to releasably secure over the upper and lower guides 24, 26 respectively. The padding 28, 30 may include ridges formed on an outer surface to prevent slipping. The padding 28, 30 adds comfort to the present invention. The padding 28, 30 may be made of a thermoplastic elastomer.

The connector 21 of the present invention may include a plurality of connecting positions. Each of the connecting positions forms a different internal diameter of the incontinence clamp. For example, one of the second ends includes an interlocking tooth 14 and the other of the second ends includes a plurality of interlocking teeth 22. The interlocking tooth 14 is secured in between the plurality of interlocking teeth 22, releasably connecting the second ends together. As illustrated in the Figures, the interlocking tooth 14 may protrude from the outer surface of the upper clamp arm 10. The plurality of interlocking teeth 22 may protrude from an inner surface of a tooth tab 32 extending from the second end of the lower clamp arm 18. Pressing the clamp arms 10, 18 together releasably retains the second end of the upper clamp arm 10 to the second end of the lower clamp arm 18. The interlocking tooth 14 disposed in between different interlocking teeth 22 adjusts the diameter of the incontinence clamp.

In use, the users select the guides that better correspond to their penis shape and size. Then the user assembles the guides into the clamp by sliding the guides in the slots formed in the inner surface. After assembling the guides, the user assembles the pads over the guides. Once the pads are assembled, the user opens the incontinence clamp by releasing the catch and lifting up the top arm. The user may then place the penis between the pads with the incontinence clamp about halfway down the shaft. Latch the incontinence clamp to compress the urethra at the level that's comfortable to the user. The bottom part of the clamp is designed to concentrate the pressure in the urethra while providing room to the corpora cavernosa to move on the sides. The top part of the clamp is designed to promote a correct blood circulation and sensation, enabling the dorsal arteries, veins and nerve to be in a pressure significantly lower than the applied in the urethra. Given the variety of guides and pressure levels of the clamp, the adaptation between the device and the penis is much more effective, reliable and healthier for the patient. The pads with ridges permit the correct skin perspiration and prevent slippage. Due to the flexibility of the material, the pads provide comfort to the user.

It should be understood, of course, that the foregoing relates to exemplary embodiments of the invention and that modifications may be made without departing from the spirit and scope of the invention as set forth in the following claims.

What is claimed is:

1. An incontinence clamp comprising:
   an upper clamp arm dimensioned to partially encircle a penis of a user;
   a lower clamp arm dimensioned to partially encircle the penis of the user;
   a hinge pivotably connecting a first end of the upper clamp arm with a first end of the lower clamp arm;
   a connector connecting a second end of the upper clamp arm with a second end of the lower clamp arm, the connector operable to adjustably define a selected internal diameter between the upper clamp arm and the lower clamp arm;
   a removable upper guide dimensioned to span an inner surface of the upper clamp arm, the removable upper guide having an upper attachment to removably couple the removable upper guide with the inner surface of the upper clamp arm;
   an upper padding that is shaped as a cover over the removable upper guide, exclusive of the upper attachment;
   a lower guide coupled with the lower clamp arm via a lower attachment, the lower guide having a protrusion dimensioned to concentrate a pressure on a urethra, while being configured for providing room for a corpora cavernosa to move laterally of the protrusion when the upper clamp arm and the lower clamp arm are clamped about the penis of the user; and
   a lower padding that is shaped as a cover over the lower guide, exclusive of the lower attachment.

2. The incontinence clamp of claim 1, wherein the lower padding is dimensioned to selectively adjust a size of the incontinence clamp to the penis of the user.

3. The incontinence clamp of claim 2, wherein the lower guide is formed of a rigid polymer.

4. The incontinence clamp of claim 3, wherein the rigid polymer is acrylonitrile butadiene styrene.

5. The incontinence clamp of claim 1, wherein the lower padding is releasably secured over the lower guide.

6. The incontinence clamp of claim 5, wherein the lower padding is formed of a thermoplastic elastomer.

7. The incontinence clamp of claim 6, wherein the lower padding comprises a plurality of raised ridges protruding from an outer surface of the lower padding.

8. The incontinence clamp of claim 1, further comprising:
   the protrusion extending from a medial position of a concave inner face of the lower guide, the protrusion configured to exert a pressure against a urethra of the user when the incontinence clamp is in a closed position.

9. The incontinence clamp of claim 8, wherein the upper padding is removable from the removable upper guide.

10. An incontinence clamp comprising:
    an upper clamp arm comprising a first end, a second end, and a first arcuate inner surface dimensioned to partially encircle a penis of a user;
    a lower clamp arm comprising a first end, a second end, and a second arcuate inner surface dimensioned to partially encircle the penis of the user;
    a hinge pivotably connecting the first end of the upper clamp arm with the first end of the lower clamp arm;
    a removable upper guide dimensioned to span the first arcuate inner surface, the removable upper guide comprising a curved concave inner surface, a convex outer surface, and an upper attachment removably coupling the removable upper guide with the upper clamp arm;

an upper padding shaped as a cover that is sized to be secured over the removable upper guide, exclusive of the upper attachment;

a lower guide dimensioned to span the second arcuate inner surface of the lower clamp arm, the lower guide comprising a first side portion, a second side portion and a middle portion disposed in between the first side portion and the second side portion, wherein the middle portion comprises a protrusion oriented towards the upper clamp arm, and a lower attachment coupling the lower guide with the lower clamp arm; and a lower padding shaped as a cover that is sized to be secured over the lower guide, exclusive of the lower attachment.

11. The incontinence clamp of claim 10, wherein the upper padding is removably secured over the removable upper guide and the lower padding is removably secured over the lower guide.

12. The incontinence clamp of claim 11, wherein the upper padding and the lower padding are formed of a thermoplastic elastomer.

13. The incontinence clamp of claim 11, wherein the upper padding and the lower padding each comprise a plurality of ridges formed on an outer surface.

14. The incontinence clamp of claim 10, wherein the removable upper guide and the lower guide are formed of a rigid polymer.

15. The incontinence clamp of claim 14, wherein the rigid polymer is acrylonitrile butadiene styrene.

16. The incontinence clamp of claim 10, wherein the protrusion further comprises:

a curved convex protrusion extending from a middle portion of the second arcuate inner surface.

17. The incontinence clamp of claim 10, further comprising a cooperating connector at the second end of each of the upper clamp arm and the lower clamp arm, the cooperating connector having a plurality of connecting positions, wherein each of the plurality of connecting positions couples the upper clamp arm with the lower clamp arm to adjustably form a different internal diameter of the incontinence clamp.

18. An incontinence clamp, comprising:

an upper clamp arm having an arcuate inner surface;

a lower clamp arm having an arcuate inner surface, and an outer surface;

a hinge connecting a first end of the upper clamp arm with a first end of the lower clamp arm;

an upper guide spanning a majority of the arcuate inner surface of the upper clamp arm and an upper attachment to removably couple the upper guide with the upper clamp arm;

an upper padding shaped as a cover over the upper guide;

a lower guide having a protrusion at an intermediate portion thereof, the lower guide coupled with the arcuate inner surface of the lower clamp arm;

a lower padding shaped as a cover over the lower guide; and a connector at a second end of each of the upper clamp arm and the lower clamp arm, the connector defining a plurality of connecting positions, wherein each of the plurality of connecting positions adjustably couples the upper clamp arm with the lower clamp arm and is configured to adjustably urge the protrusion to apply a first pressure against a urethra.

19. The incontinence clamp of claim 18, the lower guide further comprising:

a first side portion, a second side portion, and a middle portion disposed in between the first side portion and the second side portion, wherein the middle portion comprises a curved convex protrusion oriented towards the upper clamp arm.

20. The incontinence clamp of claim 19, wherein the upper guide and upper padding are dimensioned to apply a second pressure to a dorsal arterial and venous circulation, wherein the second pressure is less than the first pressure.

\* \* \* \* \*